US009622957B2

(12) United States Patent
Tezel et al.

(10) Patent No.: US 9,622,957 B2
(45) Date of Patent: *Apr. 18, 2017

(54) DERMAL FILLER

(71) Applicant: Allergan, Inc., Irvine, CA (US)

(72) Inventors: Ahmet Tezel, Fort Worth, TX (US); Wendy M. Blanda, Tustin, CA (US); Patrick M. Hughes, Aliso Viejo, CA (US); Scott M. Whitcup, Laguna Hills, CA (US); James N. Chang, Newport Beach, CA (US); Michael R. Robinson, Irvine, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/886,817

(22) Filed: Oct. 19, 2015

(65) Prior Publication Data

US 2016/0038396 A1 Feb. 11, 2016

Related U.S. Application Data

(63) Continuation of application No. 11/954,602, filed on Dec. 12, 2007, now Pat. No. 9,161,970.

(51) Int. Cl.
| | | |
|---|---|---|
| A61K 38/48 | (2006.01) | |
| A61K 8/66 | (2006.01) | |
| A61L 27/20 | (2006.01) | |
| A61L 27/54 | (2006.01) | |
| A61K 8/73 | (2006.01) | |
| A61Q 19/08 | (2006.01) | |
| A61K 8/64 | (2006.01) | |
| A61K 9/00 | (2006.01) | |
| A61K 47/10 | (2017.01) | |
| A61K 47/12 | (2006.01) | |
| A61K 47/36 | (2006.01) | |

(52) U.S. Cl.
CPC ............. *A61K 8/66* (2013.01); *A61K 8/64* (2013.01); *A61K 8/735* (2013.01); *A61K 38/4893* (2013.01); *A61L 27/20* (2013.01); *A61L 27/54* (2013.01); *A61Q 19/08* (2013.01); *A61K 9/0021* (2013.01); *A61K 47/10* (2013.01); *A61K 47/12* (2013.01); *A61K 47/36* (2013.01); *A61K 2800/48* (2013.01); *A61K 2800/54* (2013.01); *A61K 2800/91* (2013.01); *A61L 2300/252* (2013.01); *A61L 2300/602* (2013.01); *A61L 2400/06* (2013.01); *C12Y 304/24069* (2013.01)

(58) Field of Classification Search
None
See application file for complete search history.

(56) References Cited

U.S. PATENT DOCUMENTS

| | | | |
|---|---|---|---|
| 4,636,524 A | 1/1987 | Balazs et al. | 514/781 |
| 4,713,448 A | 12/1987 | Balazs et al. | 536/55.1 |
| 5,099,013 A | 3/1992 | Balazs et al. | 536/55.1 |
| 5,143,724 A | 9/1992 | Leshchiner et al. | 424/78.08 |
| 6,395,294 B1 | 5/2002 | Peyman | 424/427 |
| 6,688,311 B2 | 2/2004 | Hanin | 128/898 |
| 7,140,371 B2 | 11/2006 | Hanin | 128/898 |
| 7,226,972 B2 | 6/2007 | Zhao et al. | 525/61 |
| 7,234,469 B2 | 6/2007 | Hanin | 128/898 |
| 7,491,403 B2 | 2/2009 | Borodic | 424/239.1 |
| 7,691,394 B2 | 4/2010 | Borodic | 424/239.1 |
| 8,241,640 B2 | 8/2012 | Borodic | 424/239.1 |
| 8,394,783 B2 | 3/2013 | Stroumpoulis et al. | 514/54 |
| 8,394,784 B2 | 3/2013 | Stroumpoulis et al. | 514/55 |
| 8,470,337 B2 | 6/2013 | Manack et al. | 424/247.1 |
| 8,513,216 B2 | 8/2013 | Stroumpoulis et al. | 514/54 |
| 8,691,279 B2 | 4/2014 | Guillen et al. | 424/488 |
| 8,801,659 B2 | 8/2014 | Mudd et al. | 604/85 |
| 8,846,094 B2 | 9/2014 | Lyons et al. | 424/488 |
| 8,853,184 B2 | 10/2014 | Stroumpoulis et al. | 514/54 |
| 8,992,481 B2 | 3/2015 | Mudd et al. | 604/179 |
| 9,012,517 B2 | 4/2015 | Guillen et al. | 517/773 |
| 9,044,477 B2 | 6/2015 | Blanda et al. | 424/239.1 |
| 9,050,336 B2 * | 6/2015 | Blanda | A61K 9/0019 |
| 9,089,478 B2 * | 7/2015 | Whitcup | A61K 9/0019 |
| 9,161,970 B2 * | 10/2015 | Tezel | A61K 38/4893 |
| 9,220,780 B2 * | 12/2015 | Jung | A61K 9/0019 |
| 2004/0234532 A1 | 11/2004 | First | 424/184.1 |
| 2005/0065137 A1 | 3/2005 | Jani et al. | 514/171 |
| 2005/0244358 A1 | 11/2005 | Hermida Ochoa | 424/70.13 |
| 2008/0003241 A1 | 1/2008 | Marx et al. | 424/239.1 |
| 2008/0044476 A1 * | 2/2008 | Lyons | A61K 9/0019 424/488 |
| 2009/0082321 A1 | 3/2009 | Edelman et al. | 517/178 |
| 2010/0291136 A1 | 11/2010 | Jung et al. | 424/197.11 |
| 2010/0331259 A1 | 12/2010 | Haunold et al. | 514/18.3 |
| 2011/0229574 A1 | 9/2011 | Guillen et al. | 424/488 |
| 2012/0071437 A1 | 3/2012 | Stroumpoulis et al. | 514/54 |
| 2012/0141532 A1 | 6/2012 | Blanda et al. | 424/239.1 |
| 2012/0302007 A1 | 11/2012 | Katagiri et al. | 438/109 |

(Continued)

FOREIGN PATENT DOCUMENTS

| | | |
|---|---|---|
| WO | WO 2004/060384 | 7/2004 |
| WO | WO 2004/060384 A2 | 9/2004 |

OTHER PUBLICATIONS

U.S. Appl. No. 10/966,764, filed Oct. 14, 2004, Lyons et al.
U.S. Appl. No. 11/091,977, filed Mar. 28, 2005, Hughes et al.
U.S. Appl. No. 11/354,415, filed Feb. 14, 2006, Lyons et al.
U.S. Appl. No. 11/741,366, filed Apr. 27, 2007, Lyons et al.
U.S. Appl. No. 11/828,561, filed Jul. 26, 2007, Lyons et al.
U.S. Appl. No. 11/039,192, filed Jan. 19, 2005, Hughes et al.
U.S. Appl. No. 11/116,698, filed Apr. 27, 2005, Hughes et al.
U.S. Appl. No. 11/695,527, filed Apr. 2, 2007, Lyons et al.
U.S. Appl. No. 11/742,350, filed Apr. 30, 2007, Hughes et al.
Karcher, U S D E R M A T O L O G Y R E V I E W 2 0 0 7, pp. 35-36.

(Continued)

*Primary Examiner* — Nita M Minnifield
(74) *Attorney, Agent, or Firm* — Brigitte C. Phan; Ted A. Chan

(57) ABSTRACT

Improved dermal filler formulation comprising a hyaluronic acid and a botulinum toxin.

**

(56) References Cited

U.S. PATENT DOCUMENTS

Figure 1:
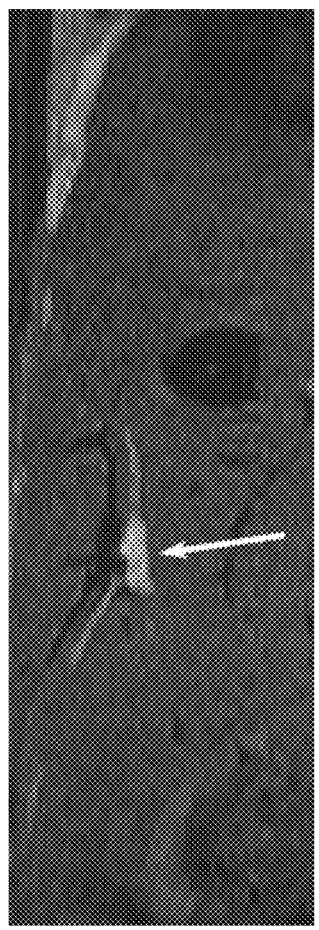

| | | |
|---|---|---|
| 2013/0040895 A1 | 2/2013 | Robinson et al. ............ 514/20.5 |
| 2013/0129790 A1 | 5/2013 | Alexis et al. ................. 424/400 |
| 2013/0136780 A1 | 5/2013 | Tezel et al. ................... 424/401 |
| 2014/0161783 A1 | 6/2014 | Jung et al. .................... 424/94.3 |
| 2014/0206774 A1 | 7/2014 | Guillen et al. ................ 514/773 |
| 2014/0302007 A1 | 10/2014 | Blanda et al. ............. 424/94.67 |
| 2014/0356438 A1 | 12/2014 | Whitcup et al. .............. 424/489 |
| 2016/0038396 A1* | 2/2016 | Tezel ..................... A61L 27/20 424/94.67 |
| 2016/0206710 A1* | 7/2016 | Jung .................... A61K 9/0019 |

OTHER PUBLICATIONS

Olenius, Aesth. Plasti. 1998, 22:97-101.
Jeon et al, Carbonhydrate Polymers 70 (2007) 251-257.
Rohrich et al, Plast. Reconstr. Surg. 120 (Suppl.: 41S-49S, Nov. 2007.).
Allergan BOTOX prescribing Information, 2012, 15 pages.
Brandt et al, In: Facial Plastic Surgery Clinics of North America, 2007, pp. 63-76.
Allemann et al, Clinical Interventions in Aging, 2008, 3/4:629-634.
Carruthers et al, Dermatol Surg 2003;29:539-544.
Carruthers et al (Dermatol Surg, 2003; 29:802-809).
Klein et al (Plastic and Reconstructive Surgery Supplement, Nov. 2007, p. 81S-88S).
Carruthers et al (Dermatol Surg, 2003,; 29:802-809).
Leslie Baumann, MD, Dermal Fillers, CHapter 23, Data obtained from www.surgery.org. 2012.
Carruthers A. et al., *The treatment of glabellar furrows with botulinum A exotoxin*, J Dermatol Surg Oncol Jan. 1990;16(1):83.
Dressler D. et al., *Electromyographic quantification of the paralysing effect of botulinum toxin in the sternocleidomastoid muscle*, Eur Neurol 2000; 43: 13-16.
Fridlund A. et al., *Guidelines for Human Electromyographic Research*, Psychophysiology 1986; 23(5): 567-590.
Grove, G.L., et al, *Objective method for assessing skin surface topography noninvasively*, chapter one, pp. 1-32 of Cutaneous Investigation in Health and Disease, edited by Leveque J-L., Marcel Dekker, Inc. (1989).
Grove G.L., et al., *Skin replica analysis of photodamaged skin after therapy with tretinoin emollient cream*, J Am Acad Dermatol 1991; 25(2) (part 1): 231-237.
Guerrissi J. et al., *Local injection into mimetic muscles of botulinum toxin A for the treatment of facial lines*, Ann Plast Surg 1997;39(5):447-53.
Harrison's Principles of Internal Medicine (1998), edited by Anthony Fauci et al., 14$^{th}$ edition, published by McGraw Hill).
Heckmann M., et al., *Quantification of the efficacy of botulinum toxin type A by digital image analysis*, J Am Acad Dermatol 2001; 45: 508-514.
Leyden J.J., et al., *Treatment of photodamaged facial skin with topical tretinoin*, J Am Acad Dermatol 1989; 21(3) (part 2): 638-644.
Pennock J.D., et al., *Relationship between muscle activity of the frontalis and the associated brow displacement*, Plast Reconstr Surg Nov. 1999; 104(6): 1789-1797.
Tassinary L. et al., *A Psychometric Study of Surface Electrode Placements for Facial Electromyographic Recording: I. The Brow and Cheek Muscle Regions*, Psychophysiology 1989; 26(1): 1-16.
van Boxtel A, et al., *Amplitude and bandwidth of the frontalis surface EMG: Effects of electrode parameters*, Psychophysiology 1984; 21(6) : 699-707.
Vitti M, et al., *Electromyographic Investigation of Procerus and Frontalis Muscles*, Electromyogr. Clin. Neurophysiol. 1976, 16: 227-236.

\* cited by examiner

DERMAL FILLER

RELATED APPLICATION

This application is a divisional application of U.S. patent application Ser. No. 11/954,602, filed Dec. 12, 2007, now U.S. Pat. No. 9,161,970, which is hereby incorporated herein by reference in its entirety; and is also related to U.S. patent application Ser. No. 11/828,561 filed Jul. 27, 2007.

BACKGROUND

The present invention relates to an improved dermal filler. In particular the present invention relates to an injectable, high viscosity dermal filler formulated with a botulinum toxin.

A pharmaceutical composition (synonymously a formulation or a composition) is a formulation which contains at least one active ingredient (for example a botulinum neurotoxin) as well as, for example, one or more excipients, buffers, carriers, stabilizers, preservatives and/or bulking agents, and is suitable for administration to a human patient to achieve a desired effect or result. The pharmaceutical compositions disclosed herein have cosmetic utility.

Movement of the face due to contractions of muscles underlying the skin can result in facial wrinkles. For example, repeated elevation of the brow by contraction of the frontalis muscle can cause brow furrows. Dermal fillers made from various substances have been used to treat facial wrinkles. Collagen based dermal fillers include Zyderm, Zyplast, Cosmoderm, Cosmoplast and Autologen. Polylactic acid dermal fillers include Sculptra™. Calcium hydroxyl apatite dermal fillers include Radiesse™. Hyaluronic acid dermal fillers include Hylaform®, Restylane® and Juvederm™. Juvederm™ (Allergan, Inc., Irvine, Calif.) comprises a sterile, biodegradable, non-pyrogenic, viscoelastic, clear, colorless, homogenized gel consisting of cross-linked hyaluronic acid formulated at a concentration of 24 mg/ml in a physiologic buffer.

Electromyographic methods have been used to study the activity of various facial muscles which can cause facial wrinkles. See e.g. Fridlund A. et al., *Guidelines for Human Electromyographic Research*, Psychophysiology 1986; 23(5): 567-590; Vitti M, et al., *Electromyographic Investigation of Procerus and Frontalis Muscles*, Electromyogr. Clin. Neurophysiol. 1976, 16: 227-236, and; Tassinary L. et al., *A Psychometric Study of Surface Electrode Placements for Facial Electromyographic Recording: I. The Brow and Cheek Muscle Regions,* Psychophysiology 1989; 26(1): 1-16.

In particular, electromyography, including surface electromyography (sEMG) has been used to investigate activity of the frontalis muscle and resultant brow displacement. See e.g. van Boxtel A, et al., *Amplitude and bandwidth of the frontalis surface EMG: Effects of electrode parameters*, Psychophysiology 1984; 21(6) : 699-707, and; Pennock J. D., et al., *Relationship between muscle activity of the frontalis and the associated brow displacement*, Plast Reconstr Surg November 1999; 104(6): 1789-1797.

Additionally, it is known to study skin topography (i.e. facial wrinkles) by making a silicone rubber negative replica (a mold) of a skin surface area. The mold captures three dimensional details of the skin surface and computerized image analysis of skin line density, depths and length analysis shown can be carried out thereon. Grove, G. L., et al, *Objective method for assessing skin surface topography noninvasively*, chapter one, pages 1-32 of Cutaneous Investigation in Health and Disease, edited by Leveque J-L., Marcel Dekker, Inc. (1989). The same silicone rubber impression method has been used to examine the effect of a topical cream to treat photodamaged skin, as by reduction of periorbital (crows feet) wrinkles. Leyden J. J., et al., *Treatment of photodamaged facial skin with topical tretinoin*, J Am Acad Dermatol 1989; 21(3) (part 2): 638-644, and; Grove G. L., et al., *Skin replica analysis of photodamaged skin after therapy with tretinoin emollient cream*, J Am Acad Dermatol 1991; 25(2) (part 1): 231-237. See also U.S. Pat. Nos. 6,688,311; 7,234,469, and; 7,140,371.

Hyaluronic Acid

Hyaluronic acid (also called hyaluronan or sodium hyaluronate) is a naturally occurring polysaccharide found in joints, connective tissue and the eye. Hyaluronic acid is a glycosaminoglycan (a mucopolysaccharide) which is a long unbranched polysaccharide composed of repeating dimeric units of glucuronic acid and N acetyl glucosamine. U.S. Pat. Nos. 4,636,524; 4,713,448; 5,099,013, and 5,143,724 disclose particular hyaluronic acids and methods for making them.

Hyaluronic acid has known therapeutic and cosmetic uses. For example, intra-articular use of hyaluronic acid as a viscosupplement to treat osteoarthritis joint pain is known (eg Orthovisc® (Anika), Durolane (Smith & Nephew), Hyalgan® (Sanofi), Hylastan® (Genzyme), Supartz® (Seikagaku/Smith & Nephew)), Synvisc® (Genzyme), and Euflexxa®, (Ferring)). Hyaluronic acid is also used cosmetically as an injectable soft tissue dermal filler (eg Juvederm™ (Allergan)) to treat facial rhytides.

The duration of the wrinkle alleviating effect of action of a dermal filler is typically about one year or less, and can be only a few months for eg dermal fillers administered in a perioral area. The duration of the wrinkle alleviating effect of action of a hyaluronic acid dermal filler is influenced by mechanical stress upon enzymatic degradation of the hyaluronic acid, as well as by the rate of clearance of the hyaluronic acid from the site of injection via the extensive tissue lymphatic vessels. Mechanical stress degradation of the injected hyaluronic acid is especially notable in areas of the face which experience frequent muscle contraction, such as around the mouth, eyes and the forehead. In particular, the dermis overlying the orbicularis oris muscle in the perioral area is a site of high mechanical stress due to frequent muscle contraction. Such repetitive mechanical stress can lead to movement of the injected hyaluronic acid from the intended site of action and untimely (premature) degradation of the dermal filler polymer.

U.S. patent applications which disclose use of therapeutic agent formulated with a hyaluronic acid include application Ser. Nos. 10/966,764, filed Oct. 14, 2004, 11/091,977, filed Mar. 28, 2005, 11/354,415, Feb. 14, 2006, 11/741,366, filed Apr. 27, 2007, 11/828,561, filed Jul. 26, 2007, 11/039,192, filed Jan. 19, 2005, 11/116,698, filed Apr. 27, 2005, 11/695,527, filed Apr. 2, 2007, and 11/742,350, filed Apr. 30, 2007.

Botulinum Toxin

The anaerobic, gram positive bacterium *Clostridium botulinum* produces a potent polypeptide neurotoxin called botulinum neurotoxin toxin which causes a neuroparalytic illness in humans and animals referred to as botulism. Botulinum toxin type A is the most lethal natural biological agent known to man. About 50 picograms of a commercially available botulinum toxin type A (purified neurotoxin complex)[1] is a $LD_{50}$ in mice (i.e. 1 unit). One unit of BOTOX® contains about 50 picograms (about 56 attomoles) of botulinum toxin type A complex. One unit (U) of botulinum toxin is defined as the $LD_{50}$ upon intraperitoneal injection into female Swiss Webster mice weighing 18 to 20 grams each.

[1] Available from Allergan, Inc., of Irvine, Calif. under the tradename BOTOX® in 100 unit vials)

Seven, generally immunologically distinct botulinum neurotoxins have been characterized, these being respectively botulinum neurotoxin serotypes A, B, $C_1$, D, E, F and G each of which is distinguished by neutralization with type-specific antibodies. The different serotypes of botulinum toxin vary in the animal species that they affect and in the severity and duration of the paralysis they evoke. Botulinum toxin apparently binds with high affinity to cholinergic motor neurons, is translocated into the neuron and blocks the release of acetylcholine.

Botulinum toxins have been used for the treatment of various therapeutic and cosmetic conditions. A botulinum toxin type A (Allergan, Inc., BOTOX®) has been approved by the U.S. Food and Drug Administration for the treatment of blepharospasm, strabismus, cervical dystonia, hyperhidrosis and glabellar lines.

The molecular weight of the neurotoxic component of a botulinum toxin complex is about 150 kD. Botulinum toxin is typically made by the Clostridial botulinum bacterium as a complex comprising the 150 kD botulinum toxin protein molecule and associated non-toxin proteins. Thus, a botulinum toxin type A complex can be produced by Clostridial bacterium as 900 kD, 500 kD and 300 kD complex forms.

It is known that injection of a botulinum toxin into facial muscles can, by weakening the injected muscles, result in a decrease of hyperkinetic wrinkles in the skin overlying the paralyzed muscles. See e.g. Carruthers A. et al., *The treatment of glabellar furrows with botulinum A exotoxin*, J Dermatol Surg Oncol 1990 January; 16(1):83. Thus, botulinum toxin has been injected into facial muscles, such as the orbicularis oculis, corrugator supercilii and frontalis muscles for the cosmetic purpose of reducing certain facial wrinkles, and it is known to use electromyographic and/or photographic techniques to assess the efficacy of such injections. Guerrissi J. et al., *Local injection into mimetic muscles of botulinum toxin A for the treatment of facial lines*, Ann Plast Surg 1997; 39(5):447-53. Electromyography has also been used to assess the effect of injection of a botulinum toxin into the sternocleidomastoid muscle for treatment of cervical dystonia. Dressler D. et al., *Electromyographic quantification of the paralysing effect of botulinum toxin in the sternocleidomastoid muscle*, Eur Neurol 2000; 43: 13-16. In sEMG the surface electrodes are placed at fixed distances from the injection point, typically 1 cm and 3 cm from the injection point. The surface electrodes can be used to measure the amplitude and area of a compound muscle action potential (CMAP) during maximal voluntary contraction of the injected muscle. One expects to find that CMAP decreases with the onset of muscle paralytic effect and to increase as the paralytic effect wears off.

Photographic methods, such as digital image analysis, have been used to determine efficacy of a botulinum toxin to treat hyperkinetic facial lines. Heckmann M., et al., *Quantification of the efficacy of botulinum toxin type A by digital image analysis*, J Am Acad Dermatol 2001; 45: 508-514.

A commercially available botulinum toxin containing pharmaceutical composition is sold under the trademark BOTOX® (available from Allergan, Inc., of Irvine, Calif.). BOTOX® consists of a purified botulinum toxin type A complex, albumin and sodium chloride packaged in sterile, vacuum-dried form. Each vial of BOTOX® contains about 100 units (U) of *Clostridium botulinum* toxin type A purified neurotoxin complex, 0.5 milligrams of human serum albumin and 0.9 milligrams of sodium chloride in a sterile, vacuum-dried form without a preservative. Other commercially available botulinum neurotoxins approved for use in humans include DYSPORT® (Beaufour Ipsen, Porton Down, England) XEOMIN® (Merz Pharmaceuticals GmbH, Frankfurt, Germany) and MYOBLOC® (Solstice Neurosciences, San Francisco, Calif.).

What is therefore needed is an improved dermal filler formulation which has a longer duration (i.e. more than three months in a perioral area) wrinkle alleviating effect upon injection (subdermal) of the dermal filler, for example by decreasing the mechanical stress and enzymatic degradation of the injected dermal filler.

SUMMARY

The present invention meets this need and provides a dermal filler formulation which has a longer duration wrinkle alleviating effect upon injection of the dermal filler.

Definitions

As used herein, the words or terms set forth below have the following definitions.

"About" means that the item, parameter or term so qualified encompasses a range of plus or minus ten percent above and below the value of the stated item, parameter or term.

"Administration" or "to administer" means the step of giving (i.e. administering) a pharmaceutical composition to a subject. The pharmaceutical compositions disclosed herein are "locally administered", that is administered at or in the vicinity of the site at which a therapeutic result or outcome is desired. For example to treat an peripheral condition by peripheral administration of a viscous formulation. "Sustained release" means release of an active agent (such as a botulinum neurotoxin) over a period of about seven days or more, while "extended release" means release of an active agent over a period of time of less than about seven days.

"Botulinum toxin" means a botulinum neurotoxin type A, B, C, D, E, F or G as either pure toxin (i.e. the about 150 kiloDalton molecular weight neurotoxic component) or as a botulinum toxin complex (about 300 to about 900 kiloDaltons molecular weight), including recombinant, chimeric, hybrid, retargeted, and amino acid sequence modified botulinum neurotoxins, but excluding botulinum toxins which are not neurotoxins such as the cytotoxic botulinum toxins $C_2$ and $C_3$.

"Entirely free" (i.e. "consisting of" terminology) means that within the detection range of the instrument or process being used, the substance cannot be detected or its presence cannot be confirmed, or that the condition, complication or side effect does not exist.

"Essentially free" (or "consisting essentially of") means that only trace amounts of the substance can be detected, or that the condition, complication or side effect is experienced by a patient for less than 10% to 20% of the time.

"Facial wrinkle" includes both a wrinkle or rhytide on the head (i.e. face, cheeks, etc) or neck as well as dermal furrows, depressions, pits, craters and sunken skin anywhere on the head or neck of a patient.

"Local administration" means administration (i.e. by a subcutaneous, intramuscular, subdermal or transdermal route) of a pharmaceutical agent to or to the vicinity muscle or a subdermal location by a non-systemic route. Thus, local administration excludes systemic (i.e. to the blood circulation system) routes of administration, such as intravenous or oral administration. Peripheral administration means administration to the periphery (i.e. to a location on or within a face, limb, trunk or head of a patient) as opposed to a visceral or gut (i.e. to the viscera) administration.

"Pharmaceutical composition" means a formulation in which an active ingredient (the active agent) can be a botulinum neurotoxin. The word "formulation" means that there is at least one additional ingredient in the pharmaceutical composition besides the active agent. A pharmaceutical composition is therefore a formulation which is suitable for diagnostic or therapeutic administration (i.e. by subdermal or intramuscular injection) to a subject, such as a human patient.

"Substantially free" means present at a level of less than one percent by weight of the pharmaceutical composition, or that the condition, complication or side effect is experienced by a patient less than 50% of the time.

"Sustained release" means release of an active agent (such as a triamcinolone) over a period of about seven days or more, while "extended release" means release of an active agent over a period of time of less than about seven days.

"Viscous carrier" means a biocompatible compound which when formulated with a botulinum neurotoxin provides upon in vivo local, subdermal injection of the formulation a depot from which the botulinum toxin is released from or diffuses away from at a rate slower than the rate of release or diffusion of the botulinum toxin from a purely aqueous solution of the botulinum toxin.

All the viscosity values set forth herein were determined at 25° C. (unless another temperature is specified). Additionally, all the viscosity values set forth herein were determined at a shear rate of about 0.1/second (unless another shear rate is specified).

Our invention encompasses a method for treating a facial wrinkle by administering to the patient a pharmaceutical composition comprising a botulinum neurotoxin and a viscous carrier for the botulinum neurotoxin, wherein the patient's facial wrinkles are alleviated for a longer period of time than they are by administration of a pharmaceutical composition which does not comprise a botulinum toxin. The administering can be carried out by local subdermal injection of the pharmaceutical composition. The disease or condition treated can be a dystonia (such as a cervical dystonia), blepharospasm, strabismus, spasticity, movement disorder, headache, migraine, hyperhidrosis, overactive bladder, prostate disorder, articular pathology, arthritis, facial wrinkles, and glabellar lines.

The viscous carrier can be selected from the group of viscous carriers consisting of hyaluronic acid, carbomer, polyacrylic acid, cellulose polycarbophil, polyvinylpyrrolidone, gelatin, dextrin, polysaccharide, polyacrylamide, polyvinyl alcohol, polyvinyl acetate, chitosans, alginates and derivatives and mixtures thereof. Preferably, the viscous carrier is a hyaluronic acid, such as a non-cross linked hyaluronic acid or a cross linked hyaluronic acid, or a mixture thereof. The hyaluronic acid used can be a polymeric hyaluronic acid with a molecular weight between about 10,000 Daltons and about 20 million Daltons and the concentration of hyaluronic acid in the formulation can be between about 0.1 wt % and about 99 wt %.

In our method the period of alleviation of the facial wrinkles can be determined by a method chosen for the group of method consisting of facial mould, electromyographic (EMG) recording and photography.

Significantly, the period of time of alleviation of the facial wrinkles is from about 20% to about 100% longer than the period of time the patient's facial wrinkles are alleviated by administration of a pharmaceutical composition injected in the same volume into the same patient at the same location, to treat the same facial wrinkles, and which contains the same amount of the botulinum toxin, but which does not comprise a viscous carrier.

The viscosity of the pharmaceutical composition used to practise the method set forth above can be between about 100 cps and about 300,000 cps at 25° C., at a shear rate of 0.1/second. The botulinum neurotoxin used in our improved dermal filler can be a botulinum neurotoxin type A.

A detailed embodiment of a method within the scope of our invention is a method for treating a facial wrinkle by local, subdermal administering to the patient a pharmaceutical composition comprising a botulinum neurotoxin type A and a polymeric, hyaluronic acid for the botulinum neurotoxin, wherein the patient's facial wrinkles are alleviated for a period of time which is from about 20% to about 100% longer than the period of time the patient's facial wrinkles are alleviated by administration of a pharmaceutical composition injected in the same volume into the same patient at the same location, to treat the same facial wrinkles, and which contains the same amount of the botulinum toxin type A, but which does not comprise the hyaluronic acid.

DRAWINGS

FIG. 1 is a two dimensional magnetic resonance image taken 6 hours after injection in an anesthetized rat with the cross-linked hyaluronic acid (Juvederm™) albumin-gadolinium contrast agent complex of Example 7. The FIG. 1 image is oriented longitudinal through the gastrocnemius muscle to show the tripennate gastrocnemius lateralis (MGL) muscle group where the injection with hyaluronic acid-contrast agent complex was performed (arrow in FIG. 1). FIG. 1 shows that there was no movement of the complex during the 6 hour anesthesia period.

Figure 2:
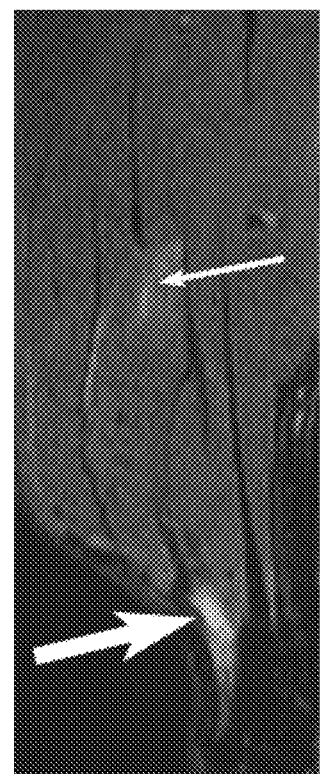

FIG. 2 is a two dimensional magnetic resonance image taken 28 hours after injection in an anesthetized rat. The FIG. 2 image is in the same orientation as FIG. 1. After the animal was awake and ambulating (i.e. causing muscle contraction in the gastrocnemius), there was migration of the hyaluronic acid-contrast agent complex from the initial site of injection (small arrow in FIG. 2) towards the Achilles tendon (large arrow in FIG. 2).

DESCRIPTION

The present invention is based on the discovery of a dermal filler-botulinum toxin formulation which can significantly increase the duration of action of a soft tissue dermal filler in areas of high mechanical stress, that is in areas of facial wrinkles.

We determined that simultaneous injection of a viscous carrier (such as a hyaluronic acid) and a botulinum toxin (such as a botulinum neurotoxin toxin type A, B, C, D, E, F or G) in a combined formulation can cause essentially immediate muscle paralysis and thereby limit mechanical stress to a polymeric viscous carrier. Other neurotoxins such as a tetrodotoxin can also be used in our improved dermal filler formulation.

The improved dermal filler formulation we developed comprises a botulinum toxin and a high viscosity, polymeric carrier for the botulinum toxin. The viscous carrier can have the characteristic of high shear thinning so that it is injectable through a 25 to 32 gauge needle.

The viscous carrier in our formulation can be a high molecular weight, polymeric, hyaluronic acid. Hyaluronic acid is a major component of the extracellular matrices of soft tissues, such as the skin and muscle. Low molecular weight (about 1000 Daltons or less) hyaluronic acid can be cleared rapidly from an intradermal or intramuscular location via the lymphatics. A higher molecular weight hyaluronic acid can have a longer tissue residence time and be eliminated from a subdermal site through lower local enzymatic process. We determined that the tissue residency time of a hyaluronic acid in soft tissues can be increased by reducing both lymphatic clearance and that this can be accomplished by increasing the biological stability of the polymer, such as by using particular methods and cross linkers to cross link a low molecular weight hyaluronic acid to thereby prepare a much higher molecular weight (1 million Daltons or higher) hyaluronic acid, which has increased biological stability (meaning that the hyaluronic acid takes longer to biodegrade), is biocompatible and functions as a depot which contains to prevent diffusion of the botulinum neurotoxin formulated with the hyaluronic acid in any amounts which exceed the amount of botulinum toxin required to saturate adjacent neuromuscular junctions.

We determined that increasing the molecular weight of the polymeric viscous carrier concomitantly increases the local botulinum neurotoxin concentration at or near the site of injection. Additionally, we determined that by increasing the degree of cross linking of the hyaluronic acid, or increasing the concentration of a hyaluronic acid in the formulation or increasing the molecular weight of the hyaluronic acid used in the formulation results in a longer tissue residence time of the formulation and reduce diffusion of the botulinum neurotoxin from the formulation to adjacent muscle groups and importantly also reduces systemic complications form the botulinum neurotoxin, as compared to injections of aqueous formulations of the same concentration of the same botulinum neurotoxin at the same subdermal injection site.

In our formulation a preferred viscous carrier is a hyaluronic acid with a molecular weight of between about 10,000 Daltons and about 20 million Daltons. A preferred total hyaluronic acid concentration of both crosslinked and uncrosslinked components in our formulation is from about 1 wt % to about 5 wt % cross linked hyaluronic acid. Where a cross linked hyaluronic acid is used the actual crosslinking density (i.e. how many of the hyaluronic acid monomers are actually linked to other hyaluronic acid monomers) is from about 5% to about 40%.

A neurotoxin, such as a botulinum neurotoxin A and/or a tetrodotoxin, can be encapsulated in the polysaccharide polymer network itself or into large vessels within the network that enable local, sustained and controlled release of actives to the surrounding tissue of the injection site. Parameters such as hyaluronic acid concentration, degree of crosslinking, median particle size, and molecular weight of the raw material hyaluronic acid can be varied to permit altered release kinetics for the neurotoxin. The encapsulation can be carried out by simple mixing or by allowing the neurotoxin to mix with the polymer network at a highly hydrated state; followed by dehydration of the network to control the release kinetics (e.g. final swelling ratio of the polymer). The contracted network can be sized into particles, mixed with the dermal filler and delivered at the site of the injection. The slow re-hydration of the neurotoxin loaded polysaccharide particles can provide a sustained and controlled delivery of the neurotoxin.

A second method of encapsulating the neurotoxin is to incorporate the active molecules into biocompatible and biodegradable vessels that could be delivered at the same time with the polymer filler. Such vessels can be composed of non-covalently or covalently linked self-assembled molecules (e.g. liposomes, polymerized vesicles).

Our improved dermal filler formulation has the following characteristics which characteristics provide an improved, injectable dermal filler gel formulation:

(1) high rheological strength (G'>300 at 5 Hz at linear viscoelastic regime);

(2) when a hyaluronic acid is used as the viscous carrier, the hyaluronic acid has in the formulation a concentration of between 20 to 40 mg/ml;

(3) the degree of cross linking of the polymer which comprises the viscous carrier is between about 1% to about 8% (w/w);

(4) the weight percent of a cross linker viscous carrier (i.e. cross-linked hyaluronic acid) in the formulation is at least 85 wt %;

(5) the raw material viscous carrier (i.e. a hyaluronic acid) has a molecular weight of between about 600 kDa and about 1,500 kDa, and;

(60 the average molecular weight of the total viscous carrier (soluble non-cross linked viscous carrier plus cross linked viscous carrier) in the final formulated improved dermal filler is greater than 400 kDa.

A viscous carrier within the scope of our invention can have a viscosity at 25° C. of at least about 10 cps or at least about 100 cps or at least about 1000 cps, more preferably at least about 10,000 cps and still more preferably at least about 70,000 cps or more, for example up to about 200,000 cps or about 250,000 cps, or about 300,000 cps or more, at a shear rate of 0.1/second. The present drug delivery systems not only have the relatively high viscosity as noted above but also have the ability or are structured or made up so as to be effectively placeable, e.g., injectable, into a posterior segment of an eye of a human or animal, preferably through a 27 gauge needle, or even through a 30 gauge needle. Low molecular weight and cross-linked hyaluronic acids exhibit little if any shear thinning and can be useful to prepare formulations within the scope of our invention, as low viscosity formulations.

The presently useful viscous carrier preferably is a shear thinning component in that as the present composition containing such a shear thinning viscous carrier is passed or injected into the posterior segment of an eye, for example, through a narrow space, such as 27 gauge needle, under high shear conditions the viscosity of the viscous carrier is substantially reduced during such passage. After such passage, the viscous carrier regains substantially its pre-injection viscosity so as to maintain the microspheres in suspension in the eye.

Any suitable viscous carrier can be used in accordance with the present invention. The viscous carrier is present in an amount effective in providing the desired viscosity to the improved dermal filler. Advantageously, the viscous carrier is present in an amount in a range of from about 0.5 wt % to about 95 wt % of the drug delivery system. The specific amount of the viscous carrier used depends upon a number of factors including, for example and without limitation, the specific viscous carrier used, the molecular weight of the viscous carrier used, the viscosity desired for the present drug delivery system being produced and/or used and like factors.

Examples of useful viscous carriers include, but are not limited to, hyaluronic acid, carbomers, polyacrylic acid, cellulosic derivatives, polycarbophil, polyvinylpyrrolidone, gelatin, dextrin, polysaccharides, polyacrylamide, polyvinyl alcohol, polyvinyl acetate, derivatives thereof and mixtures thereof.

Preferably, a dermal filler is used as the viscous carrier. Suitable dermal fillers for that purpose include collagen (sterile collagen is sold under the trade names Zyderm, Zyplast, Cosmoderm, Cosmoplast and Autologen), Hylaform® (hyaluronic acid), Restylane® (hyaluronic acid), Sculptra™ (polylactic acid), Radiesse™ (calcium hydroxyl apatite) and Juvederm™. Juvederm™, available from Allergan, Inc. (Irvine, Calif.) comprises a sterile, biodegradable, non-pyrogenic, viscoelastic, clear, colorless, homogenized gel consisting of cross-linked hyaluronic acid formulated at a concentration of 24 mg/ml in a physiologic buffer. Hyaluronic acid is a polysaccharide found in the dermis of all mammals.

The molecular weight of the presently useful viscous carrier can be in a range of about 10,000 Daltons or less to about 2 million Daltons or more. In one particularly useful embodiment, the molecular weight of the viscous carrier is in a range of about 100,000 Daltons or about 200,000 Daltons to about 1 million Daltons or about 1.5 million Daltons. Again, the molecular weight of the viscous carrier useful in accordance with the present invention may vary over a substantial range based on the type of viscous carrier employed, and the desired final viscosity of the present drug delivery system in question, as well as possibly one or more other factors.

In one very useful embodiment, the viscous carrier is a polymeric hyaluronate component, for example, a metal hyaluronate component, preferably selected from alkali metal hyaluronates, alkaline earth metal hyaluronates and mixtures thereof, and still more preferably selected from sodium hyaluronates, and mixtures thereof. The molecular weight of such hyaluronate component preferably is in a range of about 50,000 Daltons or about 100,000 Daltons to about 1.3 million Daltons or about 2 million Daltons. In one embodiment, the present compositions include a polymeric hyaluronate component in an amount in a range about 0.05% to about 0.5% (w/v). In a further useful embodiment, the hyaluronate component is present in an amount in a range of about 1% to about 4% (w/v) of the composition. In this latter case, the very high polymer viscosity forms a gel that slows particle sedimentation rate to the extent that often no resuspension processing is necessary over the estimated shelf life, for example, at least about 2 years, of the drug delivery system. Such a drug delivery system can be marketed in pre-filled syringes since the gel cannot be easily removed by a needle and syringe from a bulk container.

The improved dermal filler of our invention can be administered by any suitable method as determined by the attending physician. The methods of administration permit the improved dermal filler to be administered locally to a selected target tissue. Methods of administration include injection of a solution or composition containing the dermal filler.

The amount of the neurotoxin contained by the improved dermal filler can be varied based upon criteria such as the location of the treatment, or the solubility characteristics of the agent or formulation chosen, as well as the age, sex, weight, health of the patient and the depth and extent of the facial wrinkles to be treated. Methods for determining the appropriate route of administration and dosage are generally determined on a case by case basis by the attending physician. Such determinations are routine to one of ordinary skill in the art (see for example, *Harrison's Principles of Internal Medicine* (1998), edited by Anthony Fauci et al., 14th edition, published by McGraw Hill).

Our improved dermal filler as well as a botulinum neurotoxin can also comprise of one or more of the following non-limiting, exemplary agent (and/or formulation thereof): corticosteroid; botanical agent; wrinkle modifier; growth factor; moisturizer; peptide; antioxidant; keratolytic; retinoid; deoxyribonucleic acid; acne agent; enzyme; ascorbic acid; anticellulite; glycosaminoglycan; facial emollient, and; an anesthetic such as lidocaine.

The amount of the botulinum neurotoxin administered with the viscous carrier according to a method within the scope of our invention can vary according to the particular facial area being treated. Typically, no less about 5 units of a botulinum toxin type A (such as BOTOX® or Xeomin®) is administered per injection site (i.e. to each muscle portion injected), per patient treatment session. For a botulinum toxin type A such as DYSPORT®, preferably no less than about 20 units the botulinum toxin type A are administered per injection site and for a botulinum toxin type B such as MYOBLOC®, preferably no less than about 200 units of the botulinum toxin type B are administered per injection site. Generally, the total amount of BOTOX®, Xeomin®, DYSPORT® or MYOBLOC®, suitable for administration to a patient with an improved dermal filler according to the methods of the invention disclosed herein should not exceed about 100 units, about 400 units or about 4000-5000 units respectively, per treatment session.

EXAMPLES

The following examples illustrate aspects of our invention.

Example 1

Low Viscosity Botulinum Toxin-Hyaluronic Acid Formulation

An improved botulinum toxin-hyaluronic acid dermal filler formulation can be prepared as follows. 1 gram of 1,4-butanediol diglycidyl ether (as cross linker) is added to a 1-L aqueous solution containing 10 g hyaluronic acid (as the viscous carrier), adjusted to pH 12 while vortexing. The molecular weight of the uncross linked hyaluronic acid is about 500,000 Daltons. The reaction mixture is incubated at 60° C. for 45 minutes and neutralized with glacial acetic acid. The resulting crosslinked hyaluronic acid can have a crosslinking density of about 10%. Ten milligrams of the crosslinked hyaluronic acid is added to 1 mL of an aqueous solution containing 9 mg sodium chloride, 5 mg human albumin USP and 1,000 mouse $LD_{50}$ units of botulinum toxin type A complex. The final solution is lyophilized in a 6-mL type I glass vial. An aliquot of the lyophilized formulation containing 100 mouse LD50 units of toxin and 1 mg of the crosslinked hyaluronic acid is reconstituted with 1 mL of water for injection (WFI) or with saline for injection. The resulting solution has a hyaluronic acid concentration of about 0.1 wt % and a viscosity of about 300 cps.

Example 2

Low Viscosity Botulinum Toxin-Hyaluronic Acid Formulation with a Higher Hyaluronic Acid Concentration Another improved botulinum toxin-hyaluronic acid dermal filler formulation can be prepared as follows. 1 gram of divinyl sulfone (as cross linker) is added to a 500 mL aqueous solution containing 10 g hyaluronic acid (as the viscous carrier) adjusted to pH 14 while vortexing. The molecular weight of the uncross linked hyaluronic acid is about 200,000. The reaction mixture is incubated at 40° C. for 8 hours and neutralized with glacial acetic acid. The resulting crosslinked hyaluronic acid can have a crosslinking density of about 7%. Twenty milligrams of the crosslinked hyaluronic acid is added to 1 mL of an aqueous solution containing 9 mg sodium chloride, 5 mg human albumin USP and 1,000 mouse $LD_{50}$ units of botulinum toxin type A complex. The final solution is lyophilized in a 6-mL type I glass vial. An aliquot of the lyophilized formulation containing 100 mouse LD50 units of toxin and 1 mg the crosslinked hyaluronic acid is reconstituted with 1 mL of water for injection (WFI) or with saline for injection. The resulting solution has a hyaluronic acid concentration of about 0.5 wt % and a viscosity of about 300 cps. Since the amount of cross linking is decreased in the Example 2 formulation the concentration of the hyaluronic acid in the formulation is increased to provide the same viscosity as the Example 1 formulation.

Example 3

High Viscosity Botulinum Toxin-Hyaluronic Acid Formulation

A high viscosity botulinum toxin-hyaluronic acid dermal filler formulation can have the ingredients shown in Table 1 below.

TABLE 1

| Ingredient | Amount |
| --- | --- |
| Botulinum toxin type A | 1000 units |
| Sodium hyaluronate (polymeric) | 2.5% (w/v) |
| Sodium chloride | 0.63% (w/v) |
| dibasic sodium phosphate, heptahydrate | 0.30% (w/v) |
| Monobasic sodium phosphate, monohydrate | 0.04% (w/v) |
| Water for Injection | q.s. |
| Viscosity at shear rate 0.1/second at 25° C. | 170,000 ± 25% cps |

Preferably the botulinum toxin used is BOTOX®, which is a lyophilized, powdered form of a botulinum toxin type A stabilized with albumin and sodium chloride. The formulation is made by first reconstituting the powdered botulinum toxin with isotonic saline (sodium chloride) (thereby making part 1). The sodium hyaluronate can be purchased as a sterile powder or sterilized by filtering a dilute solution followed by lyophilization of the sodium hyaluronate to yield a sterile sodium hyaluronate powder. The sterile sodium hyaluronate is dissolved in water to make an aqueous concentrate (thereby making part 2). Part 1 and part 2 are then mixed together. Thus, the reconstituted botulinum toxin is mixed with the sodium hyaluronate concentrate to form a gel, and the phosphate buffers are then added. Water is added q.s. (quantum sufficit, as much as suffices, in this case as much as is required to prepare the homogenous mixture, dispersion, gel or suspension) and the mixture is mixed until homogenous. The formulation so prepared can be locally injected using a 27 gauge or a 30 gauge needle to provide the desired cosmetic effect.

The sodium hyaluronate powders used in the formulation has a water contents in a range of about 4% to about 20%, preferably about 4% to about 8%, by weight. Because the formulation has a density of about 1 gm/ml, the percentages set forth herein as being based on weight per volume (w/v) can also be considered as being based on weight per weight (w/w).

The formulation of Examples 3 uses a sufficient concentration of high molecular weight, sodium hyaluronate so as to form a gelatinous plug or drug depot upon local, subdermal injection of the formulation. Preferably the average molecular weight of the hyaluronate used is less than about 2 million, and more preferably the average molecular weight of the hyaluronate used is between about 1.3 million and 1.6 million. Since sodium hyaluronate solutions are subject to dramatic shear thinning, these formulations are easily injected through 27 gauge or even 30 gauge needles. Low molecular weight and cross-linked hyaluronic acids exhibit little if any shear thinning and can be useful to prepare formulations within the scope of our invention, as low viscosity formulations.

The most preferred viscosity range for the formulation is 140,000 cps to 280,000 cps at a shear rate 0.1/second at 25° C.

The formulation is formulated using excipients that are fully biocompatible (i.e. non-toxic) and is buffered at physiological pH by the low concentration of sodium phosphate salts; rendered isotonic with sodium chloride, and use Water for Injection, USP.

Example 4

Botulinum Toxin Type A-Hyaluronic Acid Dermal Filler Formulation

An improved dermal filler can be made by incorporating a neurotoxin into a crosslinked sodium hyaluronate matrix as follows. A 10-mL normal saline solution (0.9% sodium chloride) containing 50 mg albumin human USP is first prepared at room temperature. A small amount of botulinum type A neurotoxin complex, approximately 0.09 micrograms in an aqueous suspension, is then added to the saline/albumin solution (part I). Separately a 20-mL hydrogel is made with 3% crosslinked hyaluronic acid with known molecular weight and crosslinking density at pH 7.2 (part II). The part I solution is poured into the part II hydrogel, and the resulting mixture (30 mL in total weight) is gently stirred. A 1-g aliquot of the final neurotoxin-containing hydrogel is filled into a syringe and stored in a refrigerator. Alternatively, the 30-mL neurotoxin-containing hydrogel can be filled in glass vials, each with a 1-g aliquot, and lyophilized for long-term storage in a freezer.

Example 5

Tetrodotoxin-Hyaluronic Acid Dermal Filler Formulation

Another improved dermal filler can be made by incorporating a neurotoxin into a crosslinked sodium hyaluronate matrix as follows. Ten micrograms of tetrodotoxin is added into a 10-mL hydrogel containing 2% hyaluronic acid with desired molecular weight and crosslinking density or into a 10-mL sample of a commercially available, hyaluronic acid-based dermal filler (i.e. Juvederm™) that is either monophasic or particulate-based. The resulting tetrodotoxin-containing hydrogel is then stored in a glass vial with or without lyophilization.

Example 6

High Viscosity Botulinum Toxin-Hyaluronic Acid Formulation

A further improved dermal filler can be made by incorporating a neurotoxin into a crosslinked sodium hyaluronate matrix as follows. A BOTOX® vial containing 100 units of botulinum neurotoxin type A complex is reconstituted with 1 mL normal saline, which is added to 10 mL of a hydrogel containing 2.2% crosslinked hyaluronic acid with desired viscoelastic properties. The mixture is gently stirred for 10 minutes to achieve homogeneity, and is stored in a refrigerator.

Example 7

In Vivo Diffusion of Bioloqic-Hyaluronic Acid Formulations

An animal (rat) model was developed to assess the migration of hyaluronic acid in tissues. A cross-linked hyaluronic acid (Juvederm™) was complexed with the contrast agent albumin-gadolinium (MW 65,000 daltons, obtained from Biopal, Worcester, Mass.). This contract agent is visible with magnetic resonance imaging (MRI) in live animals. Previous studies have shown that the contrast agent does not diffuse out of the hyaluronic acid polymer for a minimum of 48 hours. Therefore, when a signal is visible by MRI following injection, the signal shows the location of the hyaluronic acid in the tissue.

A rat was placed under general anesthesia with an inhalational agent. A five microliter injection of the hyaluronic acid/contrast agent complex was performed with a 30 G needle in the MGL (tripennate gastrocnemius lateralis) muscle group of the gastrocnemius muscle. The needle was placed 2 cm from the heel, lateral to the tibia with an injection depth of 4-5 mm. There was no movement of the complex during the 6 hour anesthesia (FIG. 1). Since there was no contraction of the gastrocnemius muscle during anesthesia, there were no mechanical stresses to the injected area to cause migration of the hyaluronic acid/contrast agent complex. The animal was brought out of anesthesia and allowed to perform normal activities with ambulation. The animal was rescanned by MRI after 4 hours and 28 hours to determine if there was any migration of the hyaluronic acid complex with the mechanical stress of muscle contraction. The MRI scans showed movement of the hyaluronic acid/contrast agent complex once the animal was awakened and allowed to ambulate (FIG. 2). The hyaluronic acid migrated along the muscle striations and eventually moved out of the muscle to the calcaneal tendon (Achilles tendon).

The conclusions from the imaging studies were that hyaluronic acid in muscle remains in the area of injection when the muscle is paralyzed, in this case, through immobilization with general anesthesia. When muscle contraction was allowed, these mechanical stresses led to migration of the injected hyaluronic acid away from the injection site. The implication is that local paralysis of the muscle through the co-administration of a botulinum toxin with a dermal filler can increase the duration of action of the hyaluronic acid in areas of high mechanical stress, such as the perioral area.

Example 8

Facial Mould Method for Determining Extended Duration Effect of Improved Dermal Filler A female patient 46 years of age presents with bilateral, symmetrical and moderately severe forehead lines during maximum voluntary contraction of the frontalis muscle. The patient also has, with the lips together and at rest, prominent downturned mouth corners.

All make-up and cosmetics are removed from the patient's forehead, which is then cleansed with an alcohol solution. A silicon replica is made of the patients right frontalis during maximum voluntary contraction of the frontalis muscle as follows. The frontalis muscle is identified by having the patient look up and elevate her eyebrows. sEMG is used to confirm frontalis contraction. An adhesive ring 2.4 cm in diameter is positioned over an injection site on the right frontalis. A thin layer of freshly prepared silicon replica mixture (rubber silicon, 2 g, and amyl acetate catalyst, 2 drops) is applied within the adhesive ring on the right side of the forehead during maximum voluntary contraction of the frontalis muscle. The patient is instructed to maintain maximal frontalis muscle contraction for four minutes in which time the silicone polymer sets. After about 5 minutes, the hardened silicon replica is removed. The skin surface replica obtained provides a baseline negative impression (a mould) and record of the skin surface to which the silicone polymer set.

A 30 gauge syringe containing 1.5 ml of the cross linked hyaluronic acid dermal Juvederm™ filler is directed across the left side frontalis muscle fibers perpendicular to the forehead skin surface and keeping the needle-tip bevel side up, and with the frontalis at rest the Juvederm™ is injected on the left side of the forehead into the frontalis muscle, at a position 2.5 cm above the superior arch of the left eyebrow, in line with the vertical axis of the center of the pupils. At the same treatment session a separate 30 gauge syringe containing 1.5 ml of the cross linked hyaluronic acid dermal Juvederm™ filler mixed with 20 U of a botulinum toxin type A (BOTOX®) is directed across the right side frontalis muscle fibers perpendicular to the forehead skin surface and keeping the needle-tip bevel side up, and with the frontalis at rest the Juvederm™-BOTOX® mixture is injected on the right side of the patient's forehead into the frontalis muscle, at a position 2.5 cm above the superior arch of the right eyebrow, in line with the vertical axis of the center of the pupils. The patient is followed over a 104 week period subsequent to the injections and at each visit additional right frontalis silicon replicas are made.

The baseline silicon replica is compared to the subsequent series of replica obtained from the right and left sides of the patient's forehead. Thus, a silicon replica is placed on a horizontal surface on a table under a digital imaging camera held up by support. The replica is illuminated by light from a light source orientated at an angle (35° is a preferred angle) from the horizontal (and perpendicular to the major skin lines) thereby generating shadows due to the negative impressions of lines, wrinkles and furrows in the skin present on the replica surface. The digital camera is connected by means to a computer equipped with, for example, Quantirides software (version 2.0, Monaderm, Monaco). The Quantirides software can generate and analyze the imaged skin surface topography impression, as shown by the silicon replica. The following parameters can be calculated by the software: mean depth (µm), mean length (mm), total length (mm), number of wrinkles, surface area of wrinkles (depth×length; mm$^2$) and form factor (ratio length/depth) and used to obtain comparative data. The data can show that on the Juvederm™ side of the forehead the wrinkles return to their baseline topography after 9 to 12 months, but that on the Juvederm™-BOTOX® side of the forehead the wrinkles return to their baseline topography after 15 to 18 months.

The same comparative study can be carried out on a patients by left side vs right side perioral injection of either 1 ml Juvederm™ or 1 ml Juvederm™ mixed with 15 units of BOTOX® and demonstrate on the Juvederm™ perioral side the downturned mouth lines (wrinkles) return to their baseline topography after 6 to 9 months, but that on the Juvederm™-BOTOX® side of the mouth the wrinkles do not return to their baseline topography until 12-15 months post-injection.

Example 9 sEMG Method for Determining Extended Duration Effect of an Improved Dermal Filler Frontalis Muscle A male patient 54 years of age presents with bilateral, symmetrical and moderately severe forehead lines during maximum voluntary contraction of the frontalis muscle. The patient also has, with the lips together and at rest, prominent downturned mouth corners.

All make-up and cosmetics are removed from the patient's forehead, which is then cleansed with an alcohol solution. Two pairs of surface EMG electrodes placed on the left and right frontalis and the monitor of the sEMG processor is placed within the patient's field of vision to enable the amplitude of the signal to be viewed by the patient and thereby assist with maintenance of maximum voluntary contraction.

The first electrode is placed 2 cm above the brow in a vertical line with the pupil. The second electrode is positioned laterally to the first electrode at a 45-degree angle. The inter-mid-electrode distance is 1 cm. The second electrode is placed at a 45-degree angle to be parallel with the frontalis muscle fibers to increase recording accuracy. The 45-degree angle is measured using a protractor. The recording electrodes is trimmed for ease of inter electrode spacing. The ground electrodes are placed directly in front of each ear, in the s pre-auricular area.

Surface electromyographic quantification of the frontalis muscle activation is recorded using a Neuroeducator III Surface EMG Processor. The EMG processor has independent isolated channels, each with differential amplifiers to enhance the signal to noise ratio and minimize electrical noise and 50 Hertz (Hz) artifact interference. Muscle (electrical) activity is recorded using a continuous analog integrator, read by the processor at 100 times per second, with a passband of 10-1000 Hz, assuring wideband monitoring without loss of the muscle signal. The recorded sEMG signal is full-wave rectified, and the integrated sEMG recording is displayed on the screen and stored in both graphic and numerical forms.

The same sEMG processor and disposable self-adhesive, pre-gelled Ag-AgCl surface electrodes (1 cm in diameter recording area) are used for all measurements. The active and reference electrodes are identical disposable adhesive electrodes used to record the amplitude muscle activity during maximum voluntary contraction. A new set of electrodes can be used for each patient at each visit. Additional sets are used as required to maintain good adhesion to the skin of the patient and to minimize 50 hertz Hz noise.

The method of recording enables common mode rejection by the sEMG processor, a technique that minimizes crosstalk influences on the muscle activity recorded. Prior to application of the electrodes, the skin is cleansed with alcohol to minimize 50 Hz skin impedance.

sEMG is carried out during maximum voluntary contraction of the frontalis muscle using a bipolar surface recording method and the room temperature can be maintained at approximately 20° C.

The patient is sitting in an upright relaxed position facing the sEMG monitor. This positioning can allow the patient to observe their maximum amplitude signal displayed on the monitor and assist in maintaining maximum voluntary contraction for the required duration. The patient is asked raise his eyebrows to achieve the maximum target signal and sustain it at that level for 10 seconds. The sEMG signal obtained from the surface electrodes is processed by computer. The intensity of the responses is collected during maximum voluntary contraction of the frontalis muscle.

Surface Electromyography (sEMG) is carried out by comparing baseline sEMG studies with the results of serial sEMG studies following injection of a dermal filler with or without a botulinum toxin (see below) into the frontalis muscle. The amplitude ($\mu V$) of the maximum voluntary contraction for the frontalis muscle is obtained by the sEMG recording. The Neuroeducator III surface EMG processor provides an integrated sEMG amplitude value (in $\mu V$) recorded from the electrodes placed on the right and left frontalis muscle. The sEMG recording decreases as the toxin begins its paralytic effect and increases as the effect of the toxin wears off.

A 30 gauge syringe containing 1.5 ml of the cross linked hyaluronic acid dermal Juvederm™ filler is directed across the left side frontalis muscle fibers perpendicular to the forehead skin surface and keeping the needle-tip bevel side up, and with the frontalis at rest the Juvederm™ is injected on the left side of the forehead into the frontalis muscle, at a position 2.5 cm above the superior arch of the left eyebrow, in line with the vertical axis of the center of the pupils. At the same treatment session a separate 30 gauge syringe containing 1.5 ml of the cross linked hyaluronic acid dermal Juvederm™ filler mixed with 20 U of a botulinum toxin type A (BOTOX®) is directed across the right side frontalis muscle fibers perpendicular to the forehead skin surface and keeping the needle-tip bevel side up, and with the frontalis at rest the Juvederm™-BOTOX® mixture is injected on the right side of the patient's forehead into the frontalis muscle, at a position 2.5 cm above the superior arch of the right eyebrow, in line with the vertical axis of the center of the pupils. The patient is followed over a 104 week period subsequent to the injections and at each visit additional right frontalis silicon replicas are made.

The baseline sEMG is compared to the subsequent series of sEMG recordings obtained from the right and left sides of the patient's forehead. The recordings can show that on the Juvederm™ side of the forehead the wrinkles return to their baseline topography after 10 to 14 months, but that on the Juvederm™-BOTOX® side of the forehead the wrinkles return to their baseline topography after 16 to 19 months.

The same comparative study can be carried out on the patient by left side vs right side perioral injection of either 1 ml Juvederm™ or 1 ml Juvederm™ mixed with 15 units of BOTOX® and demonstrate on the Juvederm™ perioral side the downturned mouth lines (wrinkles) return to their baseline sEMG after 8 to 11 months, but that on the Juvederm™-BOTOX® side of the mouth the wrinkles do not return to their baseline topography until 14-17 months post-injection.

Example 10

Photographic Method for Determining Extended Duration Effect of an Improved Dermal Filler A female patient 61 years of age presents with bilateral, symmetrical and moderately severe forehead lines during maximum voluntary contraction of the frontalis muscle. The patient also has, with the lips together and at rest, prominent downturned mouth corners.

All make-up and cosmetics are removed from the patient's forehead, which is then cleansed with an alcohol solution.

A 30 gauge syringe containing 1.5 ml of the cross linked hyaluronic acid dermal Juvederm™ filler is directed across the left side frontalis muscle fibers perpendicular to the forehead skin surface and keeping the needle-tip bevel side up, and with the frontalis at rest the Juvederm™ is injected on the left side of the forehead into the frontalis muscle, at a position 2.5 cm above the superior arch of the left eyebrow, in line with the vertical axis of the center of the pupils. At the same treatment session a separate 30 gauge syringe containing 1.5 ml of the cross linked hyaluronic acid dermal Juvederm™ filler mixed with 20 U of a botulinum toxin type A (BOTOX®) is directed across the right side frontalis muscle fibers perpendicular to the forehead skin surface and keeping the needle-tip bevel side up, and with the frontalis at rest the Juvederm™-BOTOX® mixture is injected on the right side of the patient's forehead into the frontalis muscle, at a position 2.5 cm above the superior arch of the right eyebrow, in line with the vertical axis of the center of the pupils. The patient is followed over a 104 week period subsequent to the injections and at each visit additional photographs are taken as set forth below.

Photographs are taken of the patient before injection (baseline) and at and an regular one week intervals; for 104 weeks after injection. At each visit, digital and 35 mm photographs frontal view of the patient's upper face are taken.

The patient is positioned in the same manner for all photographs. A stereotactic device is used to ensure consistent positioning of the face in relation to the camera which comprises a dedicated chin/head support assembly. In addition, the image obtained at the screening visit (day zero) is used as a reference to ensure identical positioning of the head at all subsequent visits. Following positioning of the patient and verification of the set-up of the camera, the patient is requested to maximally elevate her eyebrows (by maximum voluntary contraction of the frontalis muscle) by viewing the fixed indicator. Three exposures of the full frontal view)(0°) of the upper face can then be taken with both a 35 mm and with a digital camera.

For all photographs lighting, framing and exposure ratios are held constant. Standardized magnification and aperture can also be used. For magnification a standardized reproduction ratio of 1:5 (35 mm equivalent) is used for both the digital and 35 mm facial photographs. The camera aperture for all 35 mm facial photographs is at f/16, and for all digital facial photographs the camera aperture is set at f/32.

The 35 mm photographic images are digitally scanned and analyzed in the same way as the digital photographs. All photographic images are calibrated and analyzed using both Mirror DPS (Canfield Scientific, Inc., Fairfield, N.J.) and Image Pro Plus (Media Cybernetics, Silver Spring, Md.). The software can draw a horizontal line through the inner canthus of the eyes and calculate the distance in millimeters between this line and the lower edge of the eyebrow at three specific points. Images from a patient are re-sized and adjusted to the same magnification as the baseline image using Mirror DPS, i.e. all images for a patient is identically sized. Images are then exported to Image Pro Plus and rotated such that a straight blue line intersects the inner canthus of the eyes.

A reduction in brow mobility (in mm) during maximal voluntary contraction is used to show onset, peak and duration of the paralytic effect. Photography is carried out by comparing baseline 2 dimensional digital (2D) and 35 mm image studies with results of serial 2D and 35 mm image studies following injection of into the frontalis muscle.

Response is determined by comparing baseline 2 dimensional digital (2D) and 35 mm image studies with results of serial 2D and 35 mm photographical image studies following injection of a dermal filler with or without a botulinum neurotoxin into the frontalis muscle (see below). The reduction of the upward mobility of the eyebrow measured during maximum eyebrow elevation is obtained using the following measurement. The parameters determined by the data from this photography analysis are onset of wrinkle attenuation, extent of wrinkle alleviation and duration of the wrinkle attenuation or alleviation.

The baseline photographs are compared to the subsequent series of photographs taken of the right and left sides of the patient's forehead. The images can show that on the Juvederm™ side of the forehead the wrinkles return to their baseline topography after 9 to 12 months, but that on the Juvederm™-BOTOX® side of the forehead the wrinkles return to their baseline topography after 15 to 18 months.

The same comparative study can be carried out on the patient by left side vs right side perioral injection of either 1 ml Juvederm™ or 1 ml Juvederm™ mixed with 15 units of BOTOX® and demonstrate on the Juvederm™ perioral side the downturned mouth lines (wrinkles) return to their baseline sEMG after 8 to 11 months, but that on the Juvederm™-BOTOX® side of the mouth the wrinkles do not return to their baseline topography until 14-17 months post-injection.

All references, articles, patents, applications and publications set forth above are incorporated herein by reference in their entireties.

Accordingly, the spirit and scope of the following claims should not be limited to the descriptions of the preferred embodiments set forth above.

We claim:

1. A method for treating a facial wrinkle by administering to the patient a pharmaceutical composition comprising a botulinum neurotoxin and a viscous carrier comprising a cross-linked hyaluronic acid, wherein the cross-linked hyaluronic acid has a cross-linking density of from 5% to about 40%; and wherein the patient's facial wrinkles are alleviated for a longer period of time than they are by administration of a pharmaceutical composition which does not comprise a botulinum toxin.

2. The method of claim 1, wherein the administering is carried out by local subdermal injection of the pharmaceutical composition.

3. The method of claim 1, wherein the period of alleviation of the facial wrinkles is determined by a method chosen for the group of method consisting of facial mould, electromyographic (EMG) recording and photography.

4. The method of claim 1, wherein the period of time of alleviation of the facial wrinkles is from about 20% to about 100% longer than the period of time the patient's facial wrinkles are alleviated by administration of a pharmaceutical composition injected in the same volume into the same patient at the same location, to treat the same facial wrinkles, and which contains the same amount of the botulinum toxin, but which does not comprise a viscous carrier.

5. The method of claim 3 wherein the hyaluronic acid is polymeric hyaluronic acid with a molecular weight between about 10,000 Daltons and about 20 million Daltons.

6. The method of claim 3 wherein the concentration of hyaluronic acid in the formulation is between about 0.1 wt % and about 99 wt %.

7. The method of claim 1 wherein the viscosity of the pharmaceutical composition is between about 100 cps and about 300,000 cps at 25° C., at a shear rate of 0.1/second.

8. The method of claim 1 wherein the botulinum neurotoxin is a botulinum neurotoxin type A.

9. A method for treating a facial wrinkle by local, subdermal administering to the patient a pharmaceutical composition comprising a botulinum neurotoxin type A and a polymeric, cross-linked hyaluronic acid for the botulinum neurotoxin, wherein the cross-linked hyaluronic acid has a cross-linking density of from 5% to about 40%; wherein the patient's facial wrinkles are alleviated for a period of time which is from about 20% to about 100% longer than the period of time the patient's facial wrinkles are alleviated by administration of a second pharmaceutical composition injected in the same volume into the same patient at the same location, to treat the same facial wrinkles, and which second pharmaceutical composition contains the same amount of the botulinum toxin type A, but which does not comprise the hyaluronic acid.

* * * * *